(12) United States Patent  (10) Patent No.: US 8,147,467 B2
Chen  (45) Date of Patent: Apr. 3, 2012

(54) NONINVASIVE LACRIMAL CANALICULAR OCCLUSION DEVICE AND METHOD

(76) Inventor: Stephen C Chen, Weston, MA (US)

( * ) Notice: Subject to any disclaimer, the term of this patent is extended or adjusted under 35 U.S.C. 154(b) by 321 days.

(21) Appl. No.: 12/566,586

(22) Filed: Sep. 24, 2009

(65) Prior Publication Data

US 2011/0071481 A1  Mar. 24, 2011

(51) Int. Cl.
*A61H 35/02* (2006.01)
*A61F 9/00* (2006.01)

(52) U.S. Cl. .................... 604/302; 606/204.25

(58) Field of Classification Search ........................ None
See application file for complete search history.

(56) References Cited

U.S. PATENT DOCUMENTS

| | | | | |
|---|---|---|---|---|
| 186,422 A * | 1/1877 | Hackett | | 128/866 |
| 497,052 A * | 5/1893 | Lamb | | 606/204.25 |
| 580,954 A * | 4/1897 | Ray | | 606/157 |
| 690,663 A * | 1/1902 | Pratt | | 128/201.11 |
| 2,015,617 A * | 9/1935 | Claudius | | 606/157 |
| 2,045,508 A * | 6/1936 | Yoe | | 351/138 |
| 2,064,986 A * | 12/1936 | Mezz | | 128/858 |
| 2,068,519 A * | 1/1937 | Speidel | | 351/103 |
| 2,620,793 A * | 12/1952 | Gollubier | | 128/858 |
| 2,681,652 A * | 6/1954 | Laxton | | 128/858 |
| 2,682,196 A * | 6/1954 | Baldanza et al. | | 351/83 |
| 3,349,771 A * | 10/1967 | Baer | | 606/157 |
| 3,446,209 A * | 5/1969 | August | | 604/302 |
| 3,463,157 A * | 8/1969 | Hunt | | 606/158 |
| D224,160 S * | 7/1972 | Bloch | | D16/326 |
| 3,729,199 A * | 4/1973 | Granberg | | 473/210 |
| 4,033,342 A * | 7/1977 | Lake | | 128/201.18 |
| 4,269,190 A * | 5/1981 | Behney | | 606/158 |
| D263,479 S * | 3/1982 | Van Exel et al. | | D16/332 |
| 4,573,982 A * | 3/1986 | Forbes et al. | | 604/300 |
| 4,685,906 A * | 8/1987 | Murphy | | 604/300 |
| 4,946,452 A * | 8/1990 | Py | | 604/301 |
| 4,960,407 A * | 10/1990 | Cope | | 604/300 |
| 5,515,872 A | 5/1996 | Martin et al. | | |
| 5,522,837 A | 6/1996 | Latina | | |
| 5,533,504 A * | 7/1996 | Stamos | | 128/201.18 |
| 5,832,930 A | 11/1998 | Martin et al. | | |
| 6,010,488 A * | 1/2000 | Deas | | 604/295 |
| 6,296,355 B1 * | 10/2001 | Rittmann | | 351/111 |
| 6,334,679 B2 * | 1/2002 | Masunaga et al. | | 351/110 |
| D476,676 S * | 7/2003 | Nielsen | | D16/326 |
| D482,384 S * | 11/2003 | Thiele et al. | | D16/328 |
| 6,641,264 B1 * | 11/2003 | Schwebel | | 351/62 |
| 6,652,094 B1 * | 11/2003 | Medana | | 351/106 |
| D495,357 S * | 8/2004 | Nielsen | | D16/328 |
| D579,112 S * | 10/2008 | Pinter | | D24/135 |
| 2001/0007493 A1* | 7/2001 | Masunaga et al. | | 351/110 |
| 2006/0129113 A1* | 6/2006 | Merrick | | 604/294 |

FOREIGN PATENT DOCUMENTS

EP  1103836 A1 * 5/2001

* cited by examiner

*Primary Examiner* — Melanie Hand
*Assistant Examiner* — Paula Craig

(57) ABSTRACT

A device enables a patient to perform non-invasive punctal occlusion by applying firm pressure to the skin external to the lacrimal canaliculi during the administration of eyedrop medicine, for the purpose of prolonging the medicine retention time. The device of this invention may be adjusted to fit the nasal aspect of the orbital rims where the lacrimal canaliculi are located. The pressure to be applied on the lacrimal canaliculi is adjustable to meet the optimal pressure requirement. The device also has a visual reference attachment that provides visual referencing points for positioning the tip of the eyedrop bottle towards the eyes. This device enables a hands-free operation and does not interfere with the wearing of eyeglasses.

4 Claims, 7 Drawing Sheets

US 8,147,467 B2

NONINVASIVE LACRIMAL CANALICULAR OCCLUSION DEVICE AND METHOD

BACKGROUND OF THE INVENTION

The present invention relates generally to medical instruments. More particularly, it relates to external pressure applicators and methods for administering eyedrop medicine. The lacrimal canaliculi (also known as tear ducts) allow tears to flow from the eye surface into the lacrimal sac and subsequently into the nasolacrimal ducts and exit through the nose into the back of the throat. The distal part of the nasolacrimal ducts are encased in bone and pressure on the skin external to that part will not impede tear drainage. Applying small pressure on the skin over any other part of the tear drainage path can effectively block tear drainage into the rest of the system. When administering eyedrop medicine on the eye, blocking this drainage path (also known as punctal occlusion) for a few minutes will enable the eye to fully absorb the medicine.

The current method of administering short-term punctal occlusion is to have the patient use a finger to press down upon the skin overlying the lacrimal canaliculi, lacrimal sac, and/or superior portion of the nasolacrimal ducts. Ophthalmologists typically prescribe 5 minutes of pressing time per eyedrop application. For example, when glaucoma patients are treated with multiple types of eyedrops, a 5 minute pressing time for each type of eyedrop would add up to a long duration of 15-20 minutes. Holding the finger for such a long duration is uncomfortable and not practical for most people. Consequently, patients seldom follow this practice as prescribed, thereby decreasing the efficacy of the treatment. Another issue is that patients seldom know exactly where the correct pressing point is located. Pressing on an incorrect area will not close the tear drainage path and therefore will not stop the eyedrop flow into the rest of tear drainage system. As a result, the retention time of eyedrop on the eye and effectiveness of the medicine is sub-optimal. This problem limits optimal treatment response leading to unnecessary prescription of additional medications, worsening disease, and risks of expensive eye surgery.

Punctal Occlusion plugs are disclosed in U.S. Pat. Nos. 6,994,684, 6,290,684, 5,830,171, 5,723,005, 5,334,137, and 5,283,063. However, all these patents involve some invasive procedures that may not be administered by patients alone. The subject matter of noninvasive external punctal occlusion is disclosed in the following patents:

U.S. Pat. No. 5,515,872 to Martin et al. discloses a clamp for placing over the nose bridge prior to ocular medication, to seal the nasolacrimal sac to prevent drainage of medication away from the eye. The clamp is positioned by a flexible molded nose cover. In one embodiment, the clamp is attached to eyeglasses designed to accept eyedrop applied to the eye. Subsequently, U.S. Pat. No. 5,832,930 was filed that added modified eyeglass frame and elastic fastening bands.

U.S. Pat. No. 5,522,837 to Latina discloses a U-shape device, with a bulbous element on the end of each leg that performs the similar function as the nose clamp except it requires hand positioning and pushing. The said device also has a pair of tubes attached to it to channel the eyedrop onto the eyes.

The nose clamp has its limitation as it may be difficult to clamp on a shallow or flat nose bridge. Positioning the pressure point right on the tear drainage path is the key to effective punctal occlusion. The flexible molded positioning device associated with the nose clamp may have difficulty to fit on the exact location on the nose as the nose boundary is somewhat fuzzy. The U-shape pressing device depends on patients to put the device on the right spot. The Martin clamp and Latina U-shape device would in no way suggest the device of this invention because they compress the nasolacrimal sac or nasolacrimal ducts on the nose rather than lacrimal canaliculi on the orbital rims.

To assure the punctal occlusion device functioning properly, a method is needed to calibrate the occlusion pressure and to verify the occlusion effectiveness. None of the prior patents disclose such method. Furthermore, it is desirable to enable patients to resume normal life activities while using the device such as wearing glasses or driving a car. None of the prior devices offer such capability.

In addition to the said punctal occlusion, there is a need to assure that the eyedrop goes into the eye. The methods and devices disclosed in the prior patents rely on passive devices to guide the eyedrop and the passive devices may come in contact with the eyedrop. A better way to guide the eyedrop is to enable the patients to see the position of the eyedrop bottle and thereby to actively aim the tip of the eyedrop bottle at the eyes.

The herein disclosed invention overcomes all the above limitations of prior devices

BRIEF SUMMARY OF THE INVENTION

The device of this invention provides hands-free, noninvasive short-term punctal occlusion, during the eyedrop administration for the purpose of prolonging medicine retention time on eyes. While wearing this device, patients are able to continue performing other activities, such as concurrently wearing a pair of eyeglasses and even driving a car which will likely increase patient's compliance with their eyedrop regimen. The path that allows tears to drain away from eyes includes the lacrimal canaliculi, lacrimal sac, and nasolacrimal duct. Applying small pressure on any of these segments, except the distal part of nasolacrimal duct, can block the tear drainage. However, it is difficulty to locate these segments as they are deeply positioned under the skin.

The device of this invention specifically blocks the lacrimal canaliculi next to the eye, unlike the prior devices that attempt to block the nasolacrimal sac or nasolacrimal ducts on the nose. As one of the important claims of this invention, the said device leverages the unique shape of the nasal aspect of the orbital rim to position the lacrimal canaliculi that lay across the orbital rim. This said orbital rim section is narrow and curved which enables the said device to fit into it precisely. The said device is adjustable to accommodate differences in nose width and contour of the said orbital rim. Beside the self-positioning capability, blocking the lacrimal canaliculi is far superior than blocking other down stream path as it enables maximum possible retention of medicine within the eyes.

The said device can not only be utilized prior to administering each eyedrop medicine to block fluid from draining away from the eye to prolong the eyedrop medicine retention time but also be used for administering multiple consecutive eyedrop medicine, provided that each eyedrop application is spaced out in 5 minute interval, or as prescribed by Ophthalmologist, and the residual medicine in the eye is wiped out by tissue, or other absorbent, prior to applying the next eyedrop.

Certain eyedrop medicines have a bitter taste. This bitter taste allows the patient to detect if the eyedrop medicine is leaking through the nose into the back of the throat. An effective punctal occlusion device should stop this leak. For non-invasive external punctal occlusion, the pressure required to close the lacrimal canaliculi is very small, the patient may preset this pressure for optimal treatment as too little pressure would not close the lacrimal canaliculi and too much pressure is unnecessary and uncomfortable. A procedure to determine the optimal pressure is to escalate the pressure exerted to the lacrimal canaliculi in each eyedrop application until the leaking taste stops. The device of this invention allows patients to experimentally set this optimal pressure. For patients using tasteless eyedrop, some eyedrop with color dye may be administered and leak be verified by an Ophthalmologist.

The device of this invention consists of a continuous iron wire frame, may be coated with plastic or other rust proofing materials, with a V-shape central segment, a pair of curved segments, frontal segments, temple segments and hook and loop fastening bands (Velcro®). The curved segment of this said device comprises the said iron wire core covered with a soft rubber tube that can be bended in a shape to fit the nasal aspect of the orbital rim to enable application of firm pressure on the lacrimal canaliculi for the purpose of performing punctal occlusion during administration of certain eyedrop medicines that require prolonged retention time. The said V-shape central segment of this device is for joining the said pair of curved segments together and the adjustable V-shape angle is for adjusting the distance between the said pair of curved segments so that the said curved segments can fit the orbital rims on each sides of the nose. The said frontal segments of this said device are to wrap around the forehead and extend into temple segments and then fastening bands. The shape of the said frontal segments can be in many different forms as long as it clears the forehead which is about 1 inch radius distance from the most concaved spot of the said curved segments. The said temples should have a length to reach the ears and have an outward angle from the frontal segments. This outward angle is to provide sufficient tension on fastening bands. This said tension is transmitted through the said device frame to become occlusion pressure on lacrimal canaliculi when the bands are fastened on the back of the head.

The device of this invention is able to position itself on top of the lacrimal canaliculi via fitting the said pair of curved segments onto the nasal aspect of the orbital rims. The occlusion pressure applied on the lacrimal canaliculi by the device of this invention is adjustable via varying the temple segment outward angles and/or fastening band length. Furthermore, this device enables hands-free operations and concurrent wearing of eyeglasses.

The device of this invention further includes a visual reference attachment that provides visual referencing points for positioning the tip of an eyedrop bottle towards the eyes. Instead of passively channeling the eyedrop towards the eyes, the said attachment enables the patient to see the exact position of their eyedrop bottle and thereby be able to actively aim the tip of the eyedrop bottle towards the eyes. This said attachment can be detached from the said device for patients who do not have problem to aim their eyedrop towards the eyes.

The current invention has many advantages over prior devices that perform similar functions:

1. The disadvantage of prior devices of pressing on nasolacrimal ducts is that the distal part of nasolacrimal ducts is encased in bone and incompressible. The superior part of the nasolacrimal ducts is outside the bone and compressible but is invisible and the exact location of this portion is uncertain to patients. Furthermore, clamping on the nose tends to slip away from the nose due to the angle shape of the nose bridge, especially for people with a very shallow or flat nose bridge.

2. The device of this device performs punctal occlusion via compressing lacrimal canaliculi on the nasal aspect of the orbital rim without any chance of misplacement. It follows the well defined contour of the nasal aspect of the orbital rims to positively fit across the lacrimal canaliculi and does not need additional positioning device.

3. The device of this invention allows adjustments to fit individual's orbital rim curvature and nose width.

4. The device of this invention enables patients to customize the lacrimal canalicular occlusion pressure via varying temple outward angle and altering fastening band length as disclosed in claim 3. The optimal occlusion pressure is determined based on a leak test method as disclosed in claim 7. The other spring based clamping device offers a few spring strength selections and does not disclose any leak test method. The hand pushed device has no pressure setting but the feel of patient's hand. Therefore, the device of this invention is far more effective in delivering the optimal punctal occlusion pressure.

5. The device of this invention can be worn concurrently with a pair of eyeglasses, none of other devices can.

6. The device of this invention, when used with a visual reference attachment, enables patients to aim the tip of the eyedrop bottle towards their eyes, none of other devices can.

The device of this invention utilizes a one wire frame construction that is easy to build, adjust, and inexpensive to commercialize. A successful commercialization of this device will revolutionize eyedrop medication procedure, reduce eye medication cost, avoid high cost on eye surgery, and eventually lower the health care costs in our society.

DETAILED DESCRIPTION OF THE INVENTION

The basic embodiment of this invention is a device that enables patients to perform noninvasive punctal occlusion to prolong eyedrop retention time on eyes. The path that allows tear to drain away from eyes includes lacrimal canaliculi, lacrimal sac, and nasolacrimal ducts. Applying pressure on skin above any one of these segments, except the distal part of nasolacrimal ducts, can block the tear drainage path. The distal part of nasolacrimal ducts are encased in bone and can not be blocked by pressure on the skin over this part of nasolacrimal ducts. Applying pressure on superior part of nasolacrimal ducts by a clamp may risk the possibility of miss-placing the clamp on the bone as there is no distinguishable feature on the nose to signify where the nasolacrimal ducts begin entering the bone. For this reason, the device of this invention applies pressure on lacrimal canaliculi instead which is clearly identifiable by following the nasal aspect of the orbital rim that concaves in a narrow space next to the eye. This unique contour of the said orbital rim enables the curved segments of the device of this invention to fit onto the said orbital rim seamlessly where the lacrimal canaliculi lay across underneath. The device of this invention is further adjustable to fit different distances between two orbital rims across the nose bridge.

Figure 1:
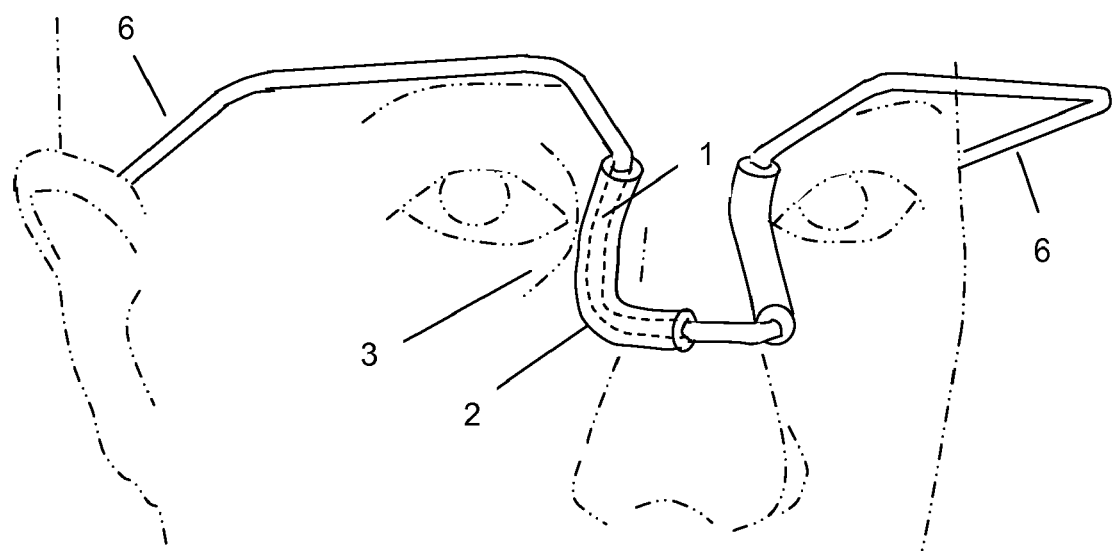
FIG. 1 is the device of this invention that fits the nasal aspect of the orbital rim.

Referring now to FIG. 1, the device of this invention is fitted onto the nasal aspect of an orbital rim 3. The said device has a pair of curved segments 1 that can be adjusted to fit the contour of the said orbital rim 3. Each curved segment 1 is an iron core, as shown in dotted line, and is sleeved with a soft rubber tube 2. The device of this invention can be worn as eyeglasses except its temples 6 are fastened with a pair of hook and loop bands (Velcro®) around the back of the head.

Figure 2:
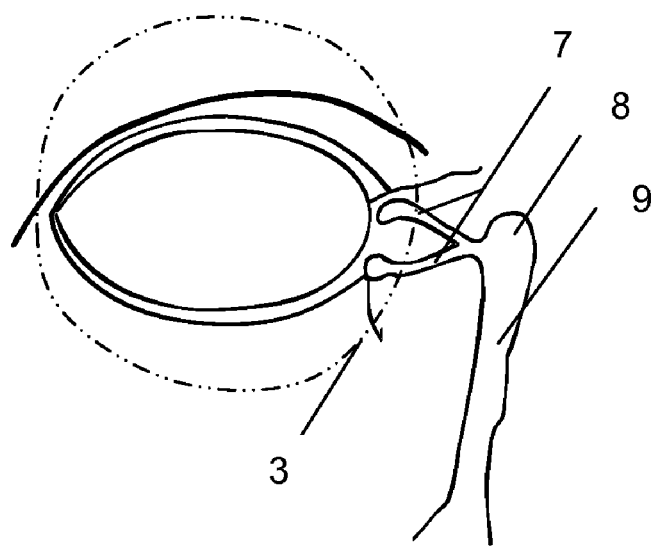
FIG. 2 is the anatomy of tear drainage path.

Referring now to FIG. 2, it shows the tear drainage path from lacrimal canaliculi 7 through lacrimal sac 8 to nasolacrimal ducts 9 and out of the nose. It also shows the nasal aspect of the orbital rim 3, which the device of this invention is based upon to locate the lacrimal canaliculi 7. The distal part of the nasolacrimal ducts are encased in bone and pressure on the skin will not affect the structures inside the bone. Furthermore, there is no distinguishable surface feature to signify where the compressible section of nasolacrimal ducts begins. The lacrimal canaliculi 7 are located next to the eye crossing the said orbital rim 3 and only a few millimeters under the skin surface. The unique shape and location of the said orbital rim enable the device of this invention to unmistakably fit onto lacrimal canaliculi.

Figure 3:
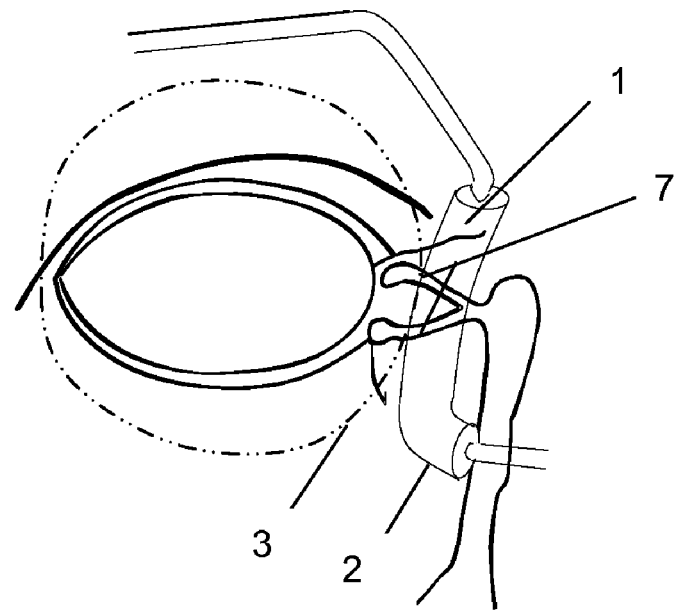
FIG. 3 is the anatomy of tear drainage path overlaid with the curved segment of the device of this invention.

Referring now to FIG. 3, it shows the anatomy of the tear drainage path overlaid with the curved segment 1 of the device of this invention. The said curved segment 1, covered with a soft rubber tube 2, is fit into the narrow space between the eye and nose and is bended concaved downward to meet the entire contour of the orbital rim 3 in that space. The rubber tube 2 is long enough to cover the entire skin contact area for wearing comfort and for assurance of crossing the lacrimal canaliculi 7 lay underneath. Through this said rubber tube 2, small pressure can be applied on the skin to effectively block the tear drainage into the rest of the system. When administering certain eyedrop medicine on the eye, blocking this drainage path for a few minutes will enable the eye to fully absorb the medicine.

Figure 4:
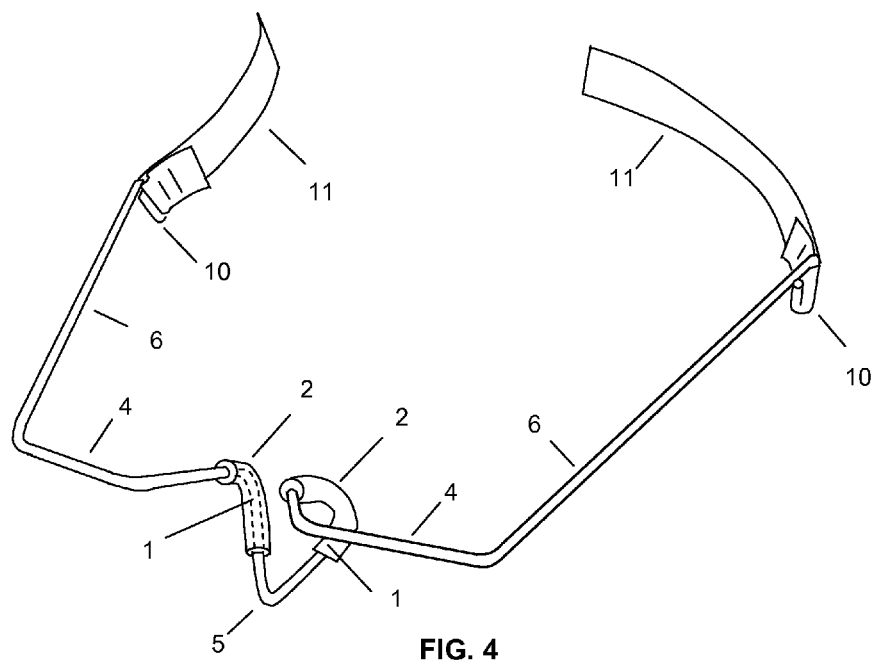
FIG. 4 is the front view of the device of this invention.

Referring now to FIG. 4, it shows the front view of the device of this invention. The said device is made out of a single continuous piece of iron wire. The wire should be soft enough to be bendable without using special tools yet strong enough to fix the structure shape while wearing the said device. The wire may be plastic coated or covered with other rust proofing materials. A pair of curved segments 1 of the said device is sleeved with soft rubber tubes 2. The said curved segments 1 are joined together by a V-shape central segment 5. The other ends of the curved segments 1 are extended forward and side way into a pair of frontal segments 4 and then angled backwards to form a pair of temples 6. At the end of each temple 6, the iron wire is bended to form a hook 10 for attaching hook and loop fastening band (Velcro®) 11.

Figure 5:
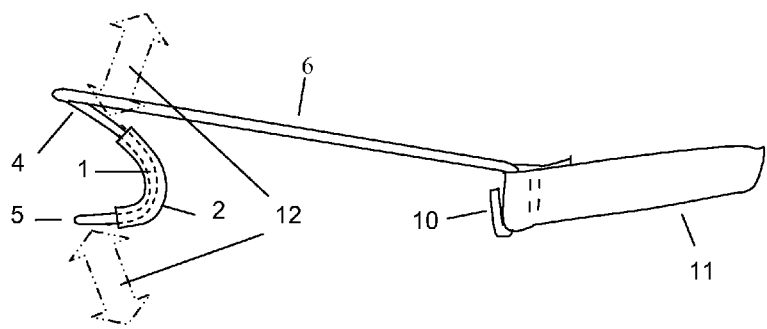
FIG. 5 is the side view of the device of this invention.

Referring now to FIG. 5, it shows the side view of the device of this invention. The curved segment 1, shown as core in dotted line, is covered by the soft rubber tube 2. The curvature of the said curved segment 1 along with rubber tube 2 can be adjusted together by applying forces in the directions as illustrated by the two-way arrows 12, to compress or expand the space between the frontal segment 4 and V-shape central segment 5.

Figure 6:
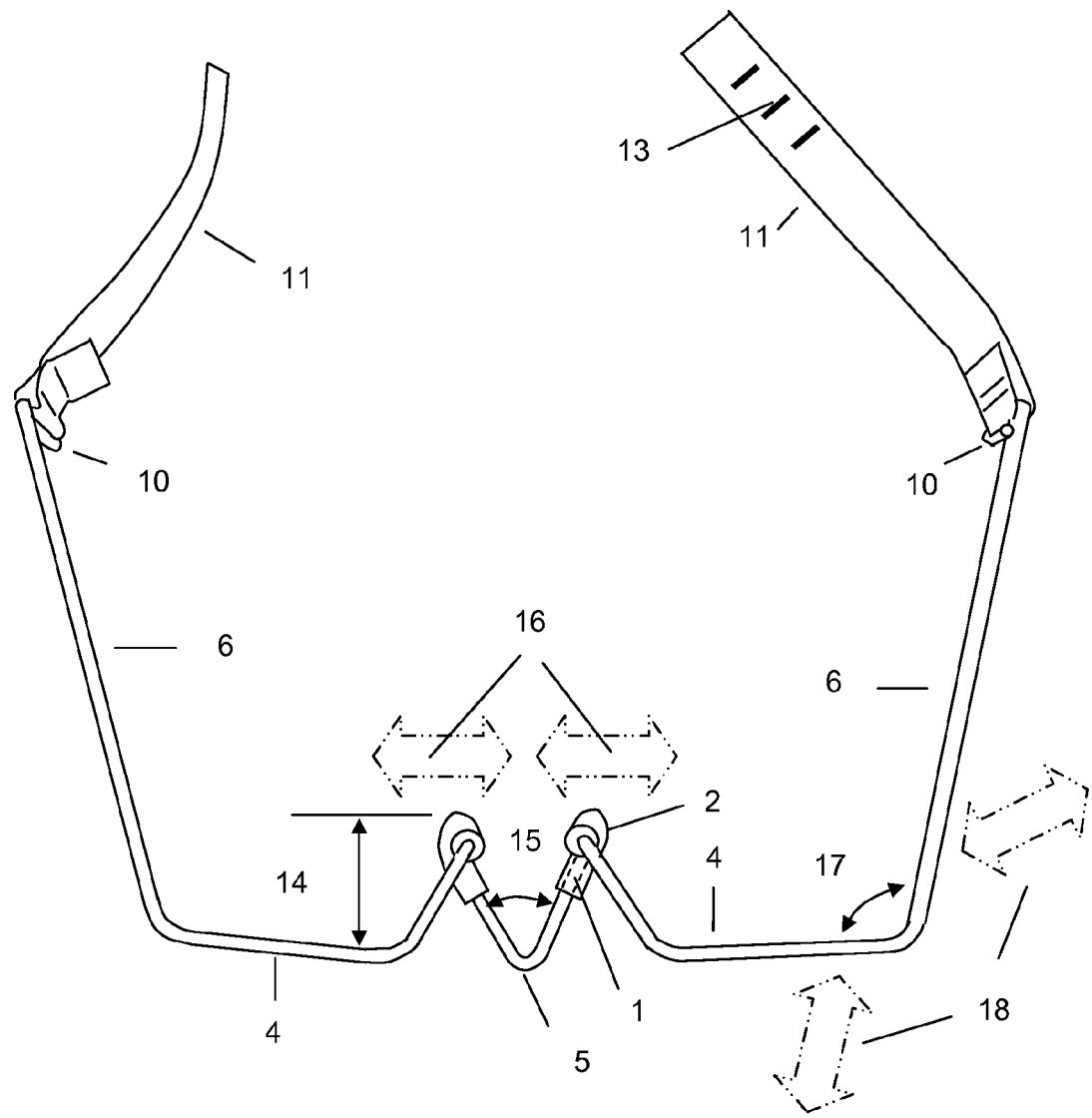
FIG. 6 is the top view of the device of this invention.

Referring now to FIG. 6, it shows the top view of the device of this invention. The tip of the V-shape central segment 5 is approximately lined up with the frontal segments 4 of the said device. The shape of the said frontal segments 4 can be in many different forms as long as it clear the forehead which is about 1 inch radius distance 14 from the most concaved spot of the said curved segments 1. The angle 15 between the V-shape central segments 5 can be widened or narrowed by applying forces in the directions indicated by two-way arrows 16 so that the curved segments 1 will fit two orbital rims across the nose. The total width of the frontal segments 4 should be similar to the frame of normal eyeglasses and the temple segments 6 should be long enough to reach the ears. The angle 17 between the frontal segment 4 and temple segment 6 should be kept in sufficient outward direction in order to provide adequate tension on the fastening bands 11 when two fastening bands 11 are attached to each other behind the head. While wearing this device, the backward pressure exerted by the head onto the fastening bands 11 will be transmitted via the device frame to become the compression pressure on the lacrimal canaliculi. This compression pressure is adjustable by varying the angle 17 and/or the length of fastening bands 11. The marks 13 on the fastening band 11 are to record the preferred band length for preferred pressure. The angle 17 can be adjusted by applying forces in the directions indicated by two-way arrows 18.

Figure 7:
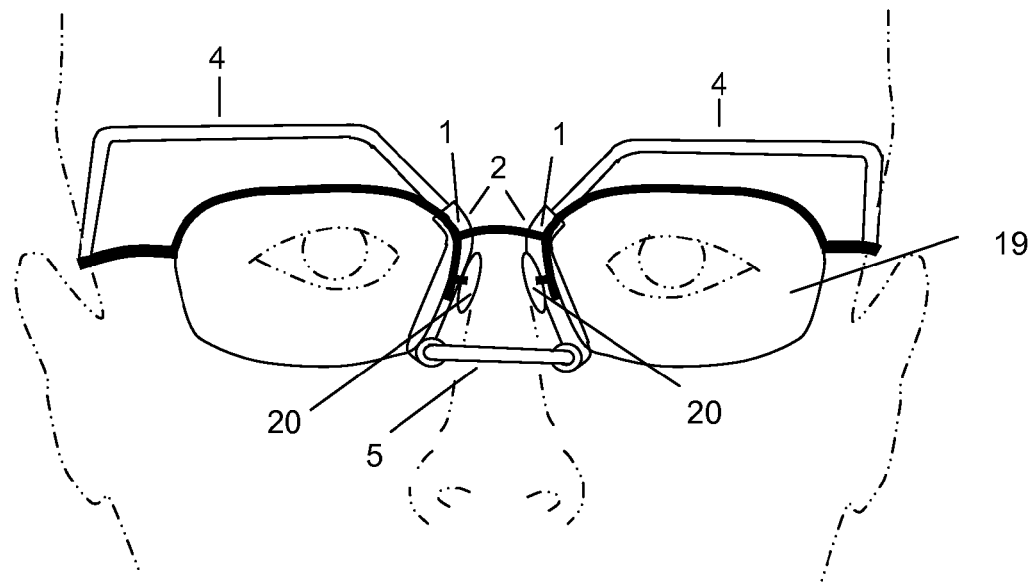
FIG. 7 is the front view of a patient wearing the device of this invention and a pair of eyeglasses.

Referring now to FIG. 7, it shows the front view of a patient wearing the device of this invention and a pair of eyeglasses 19. The patient wears the device first and then wears the eyeglasses on top of it. The nose pads 20 of the eyeglasses seats on the nose bridge above the rubber tube 2 covered curved segments 1. The frontal segments 4 are above the eyeglass 19 frame. This front view shows wearing this said device will not interfere with wearing eyeglasses.

Figure 8:
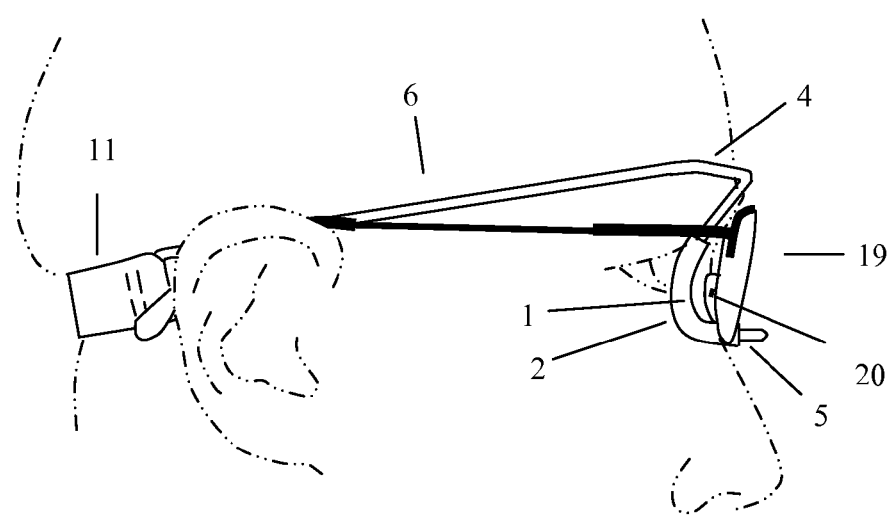
FIG. 8 is the side view of a patient wearing the device of this invention and a pair of eyeglasses.

Referring now to FIG. 8, it shows the side view of a patient wearing the device of this invention and a pair of eyeglass 19. The side view clearly shows the rubber tube 2 covered curved segment 1, is clearly behind the nose pad 20 and the frontal segment 4 is above the eyeglass 19 frame. This side view also shows wearing this said device will not interfere with wearing of eyeglasses.

Figure 9:
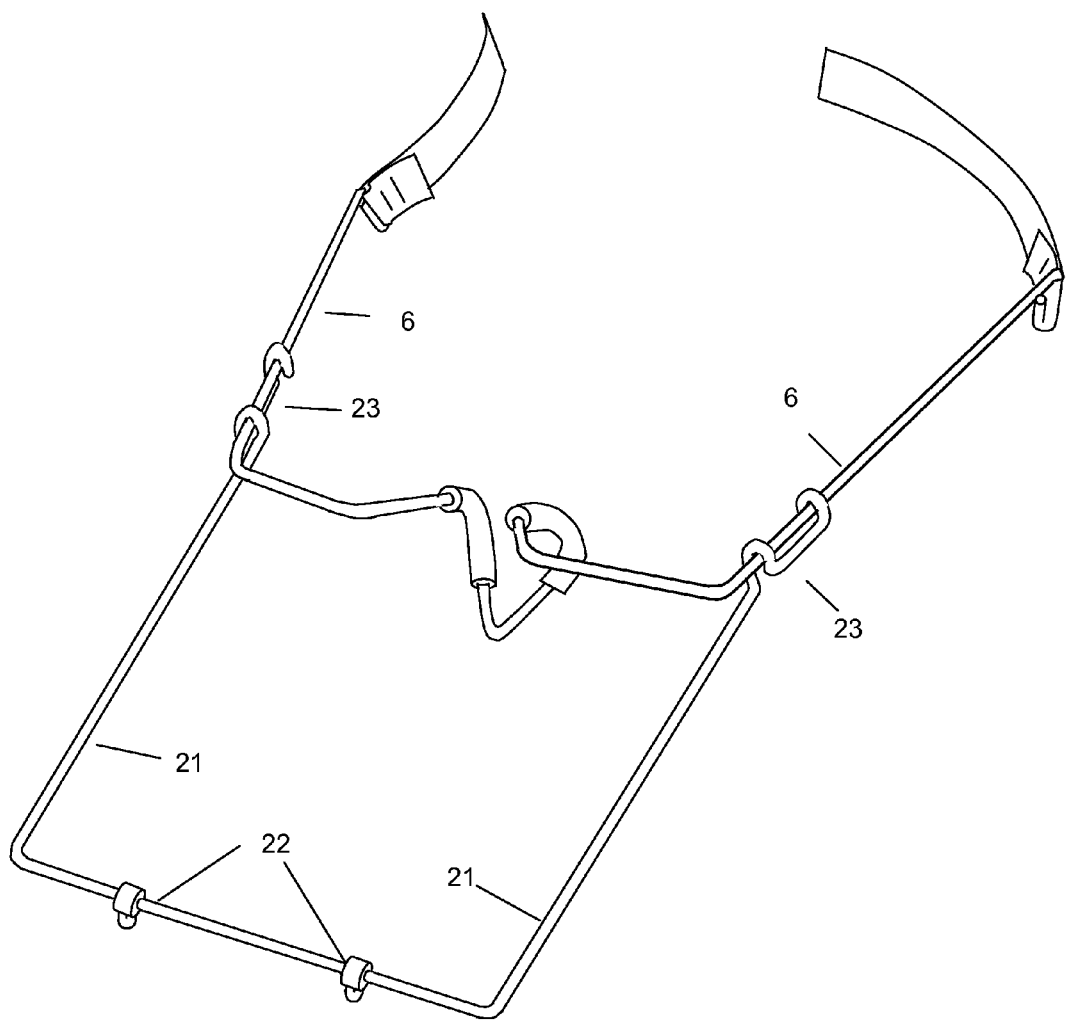
FIG. 9 is the front view of the device of this invention with a visual reference attachment.

Referring now to FIG. 9, it shows an optional embodiment that a U-shape visual reference attachment 21 is attached to the temple segments 6 of the device of this invention via a pair of clip-on hooks 23 at the ends of the U-shape frame. The front part of the said attachment has a pair of pointers 22 that provide the reference points for aiming the tip of the eyedrop bottle towards the eyes. These said pointers may slide sideway to adjust for eye positions. This said attachment 21 and pointers 22 may be made of rigid metal or plastic material.

Figure 10:
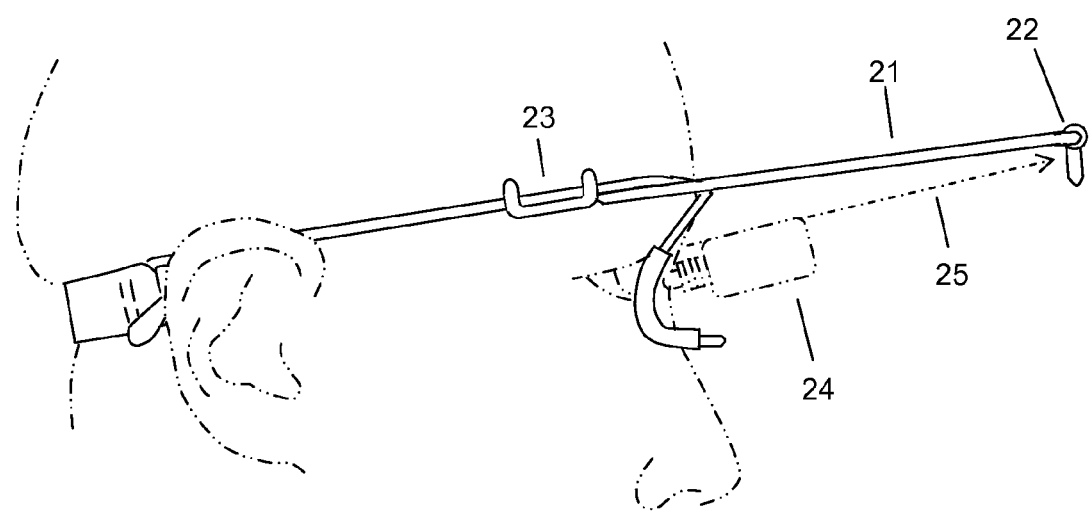
FIG. 10 is the side view of a patient wearing the device of this invention with a visual reference attachment.

Referring now to FIG. 10, it shows the side view of a patient wearing the device of this invention with the said visual reference attachment 21 attached. The upper surface of the eyedrop bottle 24 is lined up with the reference pointer 22 via a projection line 25.

The invention claimed is:

1. A device for performing punctal occlusion during administration of eyedrop medicines that require prolonged retention time, the device comprising a wire frame, the wire frame being formed from a continuous wire;

the continuous wire comprising:
a V-shaped central segment, the V-shaped central segment having an angle;
a first curved segment and a second curved segment, each of the first and second curved segments being dimensioned and configured to cross at least a part of one of the lacrimal canaliculi at the orbital rim of a patient's eye, with the central segment being located between the first curved segment and the second curved segment;

a first frontal segment and a second frontal segment, with the first and second curved segments being located between the first frontal segment and the second frontal segment;

a first temple segment and a second temple segment, each of the temple segments having an outward angle from one of the frontal segments, each of the temple segments being dimensioned and configured to extend from a temple area of the patient toward an ear of the patient, with the first and second frontal segments being located between the first temple segment and the second temple segment;

a hook and loop fastening band, the fastening band having an adjustable length, the fastening band having a first end and a second end, the first end being attached to the first temple segment, the second end being attached to the second temple segment;

the device being dimensioned and configured to apply firm pressure on the skin over the lacrimal canaliculi of a patient during administration of eyedrop medicines;

the continuous wire being configured to bend to allow adjustment of the angle of the central segment, adjustment of the curvature of the curved segments, and adjustment of the outward angle of each of the temple segments to fit the device to the patient.

2. The device according to claim 1, further comprising a pair of soft rubber tubes, each of the soft rubber tubes covering the continuous wire of one of the curved segments.

3. The device according to claim 1, wherein the device is dimensioned and configured to allow concurrent wearing of eyeglasses.

4. The device according to claim 1, wherein the device further comprises a U-shape frame, the U-shaped frame being attached to the temple segments, the U-shaped frame including a first sliding position pointer and a second sliding position pointer, each of the sliding position pointers being dimensioned and configured to provide a visual reference point for the patient in positioning a tip of an eyedrop bottle.

* * * * *